(12) United States Patent
Ragsdale

(10) Patent No.: US 8,043,838 B2
(45) Date of Patent: Oct. 25, 2011

(54) ELECTROPORATION CUVETTE WITH SPATIALLY VARIABLE ELECTRIC FIELD

(75) Inventor: Charles W. Ragsdale, Concord, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 483 days.

(21) Appl. No.: 12/366,440

(22) Filed: Feb. 5, 2009

(65) Prior Publication Data

US 2009/0209017 A1  Aug. 20, 2009

Related U.S. Application Data

(60) Provisional application No. 61/030,074, filed on Feb. 20, 2008.

(51) Int. Cl.
*C12N 13/00* (2006.01)

(52) U.S. Cl. ........... 435/173.6; 435/449; 435/450; 435/461; 435/470; 435/285.2; 435/288.1

(58) Field of Classification Search .......... 435/449, 435/450, 461, 470, 173.6, 285.2, 288.1
See application file for complete search history.

(56) References Cited

U.S. PATENT DOCUMENTS

| | | | | |
|---|---|---|---|---|
| 4,699,881 A * | 10/1987 | Matschke | ............ | 435/285.2 |
| 7,678,564 B2 * | 3/2010 | Muller-Hartmann et al. | ............ | 435/285.2 |
| 2003/0022365 A1 | 1/2003 | Marotski | | |
| 2003/0124713 A1 | 7/2003 | Ragsdale | | |
| 2005/0282265 A1 * | 12/2005 | Vozza-Brown et al. | ... | 435/285.2 |
| 2006/0281182 A1 | 12/2006 | Vozza-Brown et al. | | |

* cited by examiner

*Primary Examiner* — Bao Thuy L Nguyen

(74) *Attorney, Agent, or Firm* — Kilpatrick Townsend & Stockton LLP

(57) ABSTRACT

An electroporation cuvette is constructed with electroporation electrodes arranged in non-parallel relation to form a gap whose width varies with the location within the cuvette, plus a pair of positioning electrodes that are arranged to cause electrophoretic migration of biological cells within the cuvette according to cell size. Once the cells, suspended in a solution of the impregnant, are distributed in the cuvette by the positioning electrodes, electric field pulses are generated by the non-parallel electroporation electrodes. Because of their distribution in the cuvette, the various cells will experience voltage differentials across their widths that approach uniformity regardless of cell diameter, since the larger cells will be positioned at locations where the gap between the electrodes is greater and the smaller cells at locations where the gap is relatively small while the voltage drop across the entire gap is uniform along the length of the cell. The voltage differential across the width of the cell is thus roughly paired with the cell diameter, and this reduces the disparity in voltage differential that cells of different sizes would otherwise experience with parallel electrodes.

12 Claims, 3 Drawing Sheets

ELECTROPORATION CUVETTE WITH SPATIALLY VARIABLE ELECTRIC FIELD

CROSS-REFERENCE TO RELATED APPLICATION

This application claims the benefit of U.S. Provisional Patent Application No. 61/030,074, filed Feb. 20, 2008, the contents of which are incorporated herein by reference in their entirety.

BACKGROUND OF THE INVENTION

1. Field of the Invention

This invention lies in the field of electroporation, the process by which exogenous molecular species are inserted into membranous structures by suspending the structures in a liquid solution of the exogenous species and applying an electric field to the resulting suspension. In particular, this invention addresses electroporation cuvettes.

2. Description of the Prior Art

Electroporation, or electric pulse-driven transfection, is widely used for impregnating membranous structures, such as living biological cells, liposomes, and vesicles, with exogenous molecules. The structures are typically suspended in an aqueous solution of the exogenous species in a high-conductivity buffer. Normal saline is commonly used as the buffer since, in addition to offering relatively low resistance to an electric current, normal saline provides an environment that is favorable to the viability of most membranous structures. The suspension is typically placed in a cuvette that is equipped with electrodes, and electroporation is performed in the cuvette.

A prime concern in any electroporation procedure is efficiency, which is defined as the number of membranous structures that are successfully impregnated in the procedure. The goal is to impregnate as many membranous structures in a given sample as possible and to cause each structure to receive as closely as possible the same number of molecules of the impregnant. Full uniformity is an elusive goal, however; a certain degree of variation is inherent in any electroporation procedure, due to the different locations and physical orientations of the membranous structures relative to the electric field. When the membranous structures are biological cells, a further source of variation is the range of maturity of the cells, since a typical cell population contains cells at various stages of their life cycles. A single cell line can therefore have cells of different diameters. The electric field intensity is determined by dividing the impressed voltage by the distance between the electrodes, but the voltage across a single cell will be proportional to the cell diameter. Thus, for a given field intensity, small cells will experience a relatively low voltage difference while the voltage difference experienced by large cells will be relatively high. If the voltage difference is too low, the cell walls will not become sufficiently porous to allow the molecules to penetrate, and if the voltage difference is too high, the resulting dipole moment will cause cell lysis.

SUMMARY OF THE INVENTION

An electroporation cuvette has now been developed that addresses the variations in voltage difference experienced by cells or other membranous structures of different diameters in a single suspension. For convenience, the term "cells" is used herein to represent membranous species in general. The electrodes in the cuvette that produced the electroporation effect are configured to produce an electric field whose intensity varies with location in the cuvette, and a second pair of electrodes are incorporated into the cuvette structure to impose an electric field that will cause the cells to position themselves according to size in an arrangement that correlates with the field intensity variation. The electrodes used for positioning the cells are referred to herein as "positioning electrodes," while the electrodes used for electroporation are referred to herein as "electroporation electrodes" or "shocking electrodes." To utilize the cuvette in an electroporation procedure, the two sets of electrodes are energized in sequence, the positioning electrodes being energized first to achieve the desired spatial size distribution of the cells, and the electroporation electrodes energized second to produce electroporation with a field intensity variation that correlates with the cell size distribution. The positioning electrodes can remain energized during the electroporation, but in preferred embodiments of the invention, the voltage across the positioning electrodes will be discontinued before electroporation is begun. The electric field used in the electroporation is preferably a pulsed electric field. The voltage used in the cell positioning step will be considerably less than the voltage used in the electroporation step, by at least one order of magnitude, and more often two to three orders of magnitude.

Distribution of the cells according to size can be achieved as a direct result of the differences in the physical size of the cells, or as a result of the amount of surface charge on the cells, or a combination of both. Distribution by the amount of surface charge by itself can be achieved by the positioning electrodes themselves, while distribution by the physical size can be achieved by the positioning electrodes either alone or in conjunction with additional means such as the use of a series of sieving membranes or a sieving matrix. These and other means, embodiments, objects, and advantages of the invention are explained in further detail below.

DETAILED DESCRIPTION OF THE INVENTION AND PREFERRED EMBODIMENTS

While the features defining this invention are capable of implementation in a variety of constructions, the invention as a whole will be best understood by a detailed examination of specific embodiments. The drawings hereto represent such embodiments.

Figure 1:
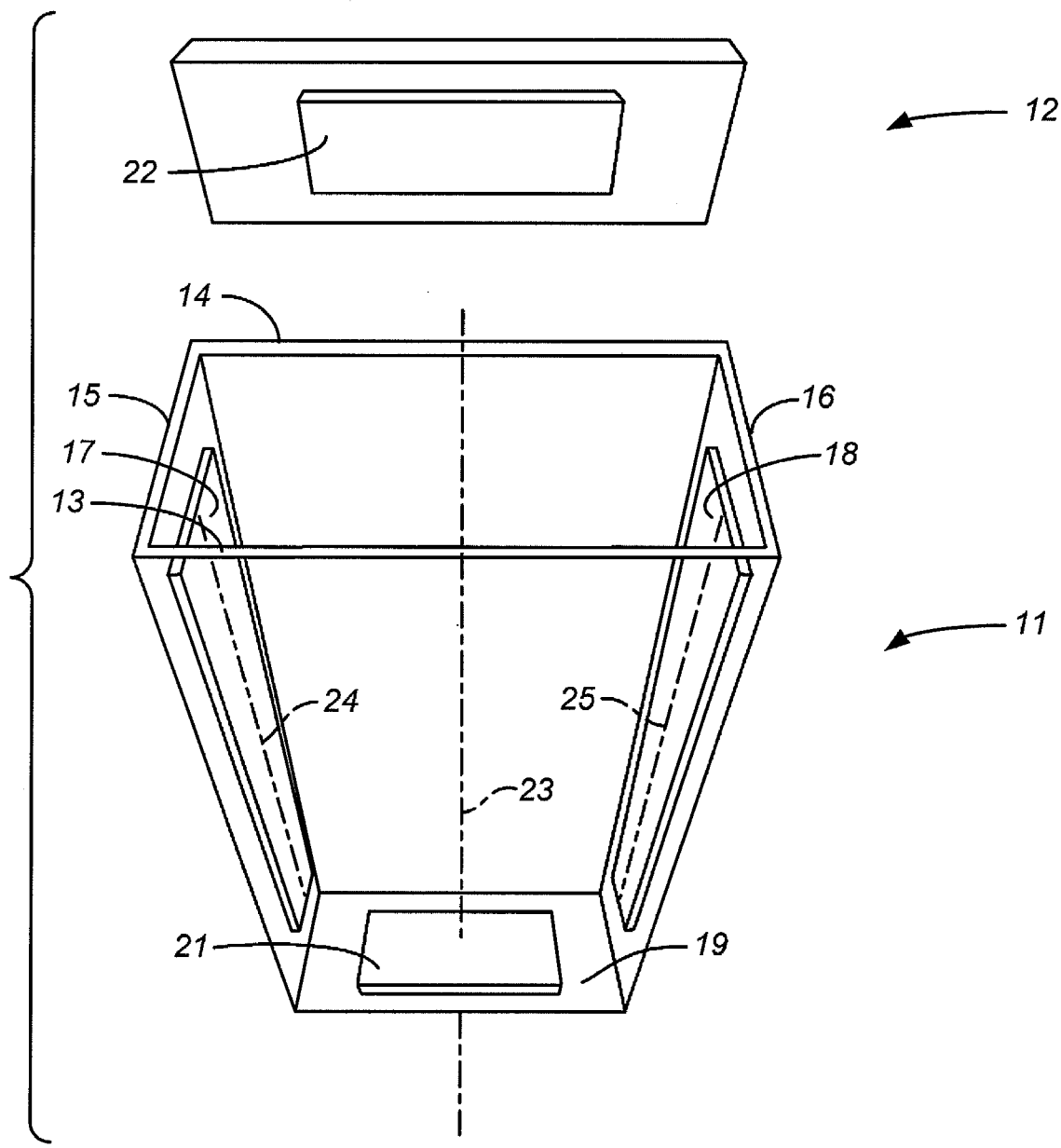
FIG. 1 is a perspective view of one example of a cuvette and lid in accordance with the present invention.

The cuvette 11 shown in FIG. 1 has an open top and a lid 12 which can be attached or separate. The cuvette 11 is rectangular in its horizontal cross section with planar walls on four sides. The front wall 13 and back wall 14 are parallel while the end walls 15, 16 are angled to form a tapering profile with the widest separation at the top and the narrowest at the base. Affixed to the two end walls and exposed to the interior of the cuvette are a pair of opposing electrodes 17, 18 which, due to the sloping walls to which they are attached, are non-parallel. These electrodes are the shocking electrodes, and due to their non-parallel arrangement, the separation between these electrodes near the top of the cuvette is greater than the separation near the base of the cuvette. Affixed to the base 19 or floor of the cuvette is a further electrode 21, and affixed to the under-side of the lid 12 is a still further electrode 22. The base and lid electrodes are the positioning electrodes.

Figure 2:
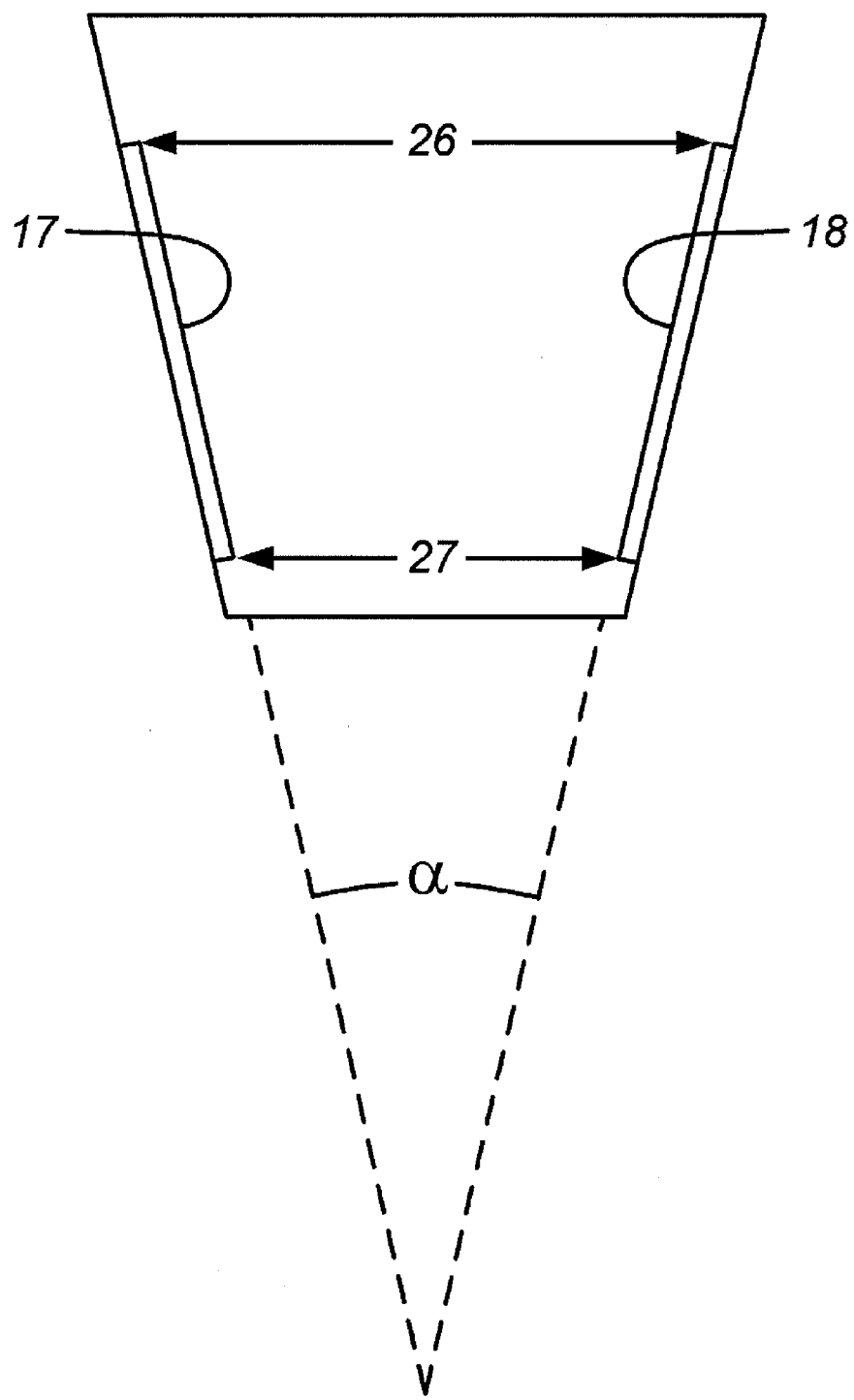
FIG. 2 is a cross section of the cuvette of FIG. 1.

The cuvette 11 is symmetrically shaped with a centerline 23, and each of the shocking electrodes 17, 18 is flat and has a centerline 24, 25. The three centerlines 23, 24, 25 are coplanar and, like the cuvette itself, the shocking electrodes are symmetrically arranged on either side of the cuvette centerline 23. FIG. 2 is a cross section of the cell and shocking electrodes along the plane of the centerlines. The angle α formed by the shocking electrode centerlines can vary and is not critical to the invention, although optimal angles will depend on the cell population and the dimensions of the cuvette. In general, preferred angles are those within the range of from about 1 degree to about 45 degrees, and most preferably from about 5 degrees to about 30 degrees. The non-parallel arrangement of the shocking electrodes can also be described in terms of the ratio of the gap 26 between the electrodes at its greatest width to the gap 27 at its narrowest width. This ratio can vary widely as well, but in most cases, an appropriate ratio is within the range of from about 1.2 to about 3.0, and preferably from about 1.3 to about 2.0. The direction of migration of the cells as they are being positioned according to size generally follows the cuvette centerline 23, which is the direction of the electric potential imposed by the positioning electrodes. The gap width between the shocking electrodes likewise decreases in the direction of the cuvette centerline 23 and, as explained below, the gradient in cell size after positioning is in the same direction with the cells decreasing in size in the same direction as the decrease in gap width of the shocking electrodes.

In an electroporation procedure utilizing the cuvette of FIGS. 1 and 2, the cuvette is filled with a buffered aqueous solution of the DNA, protein, or exogenous species in general that is used as the impregnant, and the cells to be impregnate ate placed on the exposed surface of the solution which is at the end of the cuvette 11 of greatest width. The cuvette lid 12 is then placed in the cuvette through the top opening, and pushed down far enough to assure that the lid electrode 22 is in contact with the solution. An electric potential is imposed between the lid electrode 22 and the base electrode 21. Since biological cells generally have a negative surface charge, migration of the cells downward along the direction of the cuvette centerline 23 is achieved by charging the lid electrode 22 at a negative polarity and the base electrode 21 at a positive polarity. With the electrodes thus charged, the cells migrate downward in the manner of an electrophoretic migration into the cuvette interior toward the base electrode 21. Due to their lower mass, the smaller cells will migrate at a faster rate than the larger cells. The potential is discontinued before any cells have reached the bottom of the cuvette, or a short time after the smallest cells have reached the bottom, and the result is a size gradient of the cells within the cuvette, the smaller cells having traveled a greater distance from the top due to their lower mass. The shocking electrodes 17, 18 are then pulsed, producing an electric field intensity that is greater at the bottom of the cuvette due to the narrower separation of the electrodes. The potential drop across the widths of the cells thus approaches uniformity among the range of cell sizes since the electric field intensity is itself a gradient increasing toward the bottom of the cuvette (in the direction opposite to the cell size gradient).

An alternative means of forming a cell size gradient in the cuvette 11 and lid 12 of FIG. 1, or a means of further controlling the gradient, is to place a sieving matrix in the cuvette. Agarose is one example of a sieving matrix; a suspension of beads is another example. In general, any matrix that offers resistance to the cell movement and yet contains gaps or pores of sufficient size to allow the cells to pass can serve as a sieving matrix. The matrix is immersed in a buffer solution of the impregnant, and as in the method described above, the cells are first placed on the exposed surface of the saturated or suspended matrix and the positioning electrodes are energized to induce electrophoretic migration of the cells into the matrix. Under the influence of the electric field, the cells will migrate into the matrix and distribute themselves through the matrix according to their sizes, the smaller cells migrating at a faster rate since they encounter less resistance from the matrix. The difference in migration rate can also arise from the lower mass and thus lower inertia of the smaller cells for the electrophoretic force to overcome. The migration time in this method is less critical than when the migration is performed in the absence of a sieving matrix, but time is still a factor in achieving an approximately continuous gradient from the top to the bottom of the cuvette. Appropriate or optimal migration times are readily determined by routine experimentation with observation of the resulting cell distribution. Once the desired distribution is achieved, the potential applied to the positioning electrodes is discontinued, and the shocking electrodes 17, 18 are then pulsed, producing an electric field intensity that is greater at the bottom of the cuvette due to the narrower separation of the electrodes. As in the method described above, the potential drop across the widths of the cells is approximately inversely proportional to the cell sizes since the electric field intensity is itself a gradient increasing toward the bottom of the cuvette.

Figure 3:
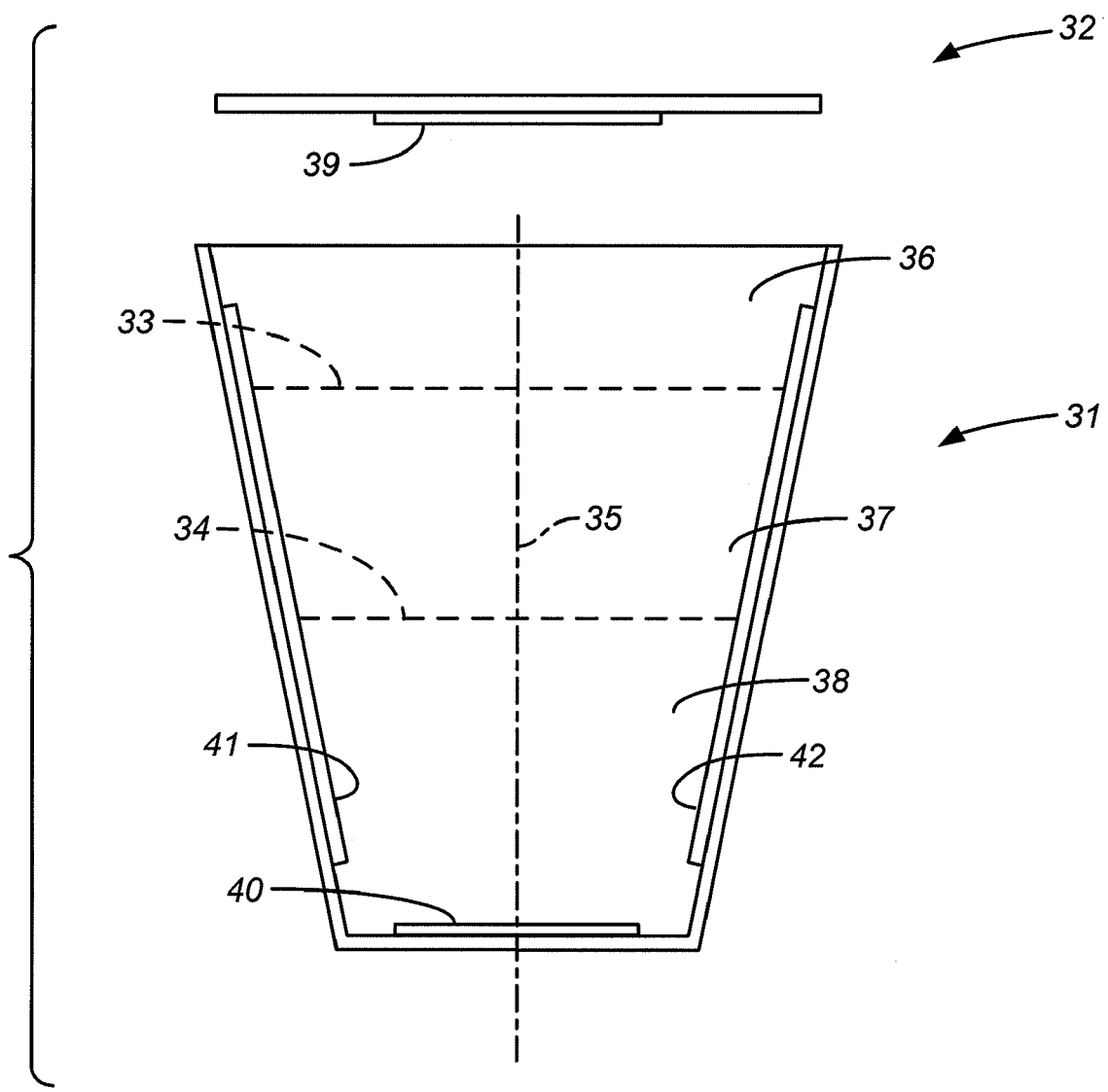
FIG. 3 is a front elevation of another example of a cuvette and lid in accordance with the present invention.

A still further means of producing and controlling a cell size gradient is achieved by the cuvette structure shown in FIG. 3. This cuvette 31 and lid 32 are identical to those of FIGS. 1 and 2 except for the additional inclusion of sieving membranes 33, 34 spanning the horizontal cross section of the cuvette. Two sieving membranes are shown in this embodiment, but the number will vary with the needs of the system, most notably the expected range of cell sizes and the size of the cuvette. Adequate size separation in some cases will thus be achieved with a single sieving membrane, although it is contemplated that in most cases two to five sieving membranes will be used. The sieving membranes are spaced apart along the longitudinal axis 35 of the cuvette and arranged such that the membrane having the largest pore size is closest to the top of the cuvette, with the pore sizes of the membranes successively decreasing toward the base of the cuvette. In the embodiment shown, the two membranes divide the cuvette interior into three chambers 36, 37, 38 arranged vertically. As in the first method described above in connection with FIG. 1, a buffered aqueous solution of the impregnant is placed in the cuvette to occupy all portions of the cuvette above and below all of the sieving membranes, and the cells are placed on the exposed surface of the solution at the top of the cuvette. The lid 32 is then placed over the cuvette to place the negative positioning electrode 39 in contact with the solution, and an electric potential is imposed between the negative positioning electrode 39 and the positive positioning electrode 40 at the base of the cuvette, causing the cells to migrate by electrophoretic means into the cuvette interior. The largest cells are retained in the upper chamber 36, mid-sized cells pass through the upper sieving membrane 33 to be retained in the middle chamber 37, and the smallest cells will pass through both sieving membranes and migrate into the lower chamber 38. The potential is maintained until the cells reach their appropriate chambers, and the separation is less time sensitive in this procedure than in either of the two procedures described above in connection with FIG. 1. The positioning potential is then discontinued, and the shocking electrodes 41, 42 are then pulsed, producing an electric field intensity that is weakest in the upper chamber 36 and successively stronger in the middle 37 and lower 38 chambers. The resulting potential drop across the widths of the cells thus inversely varies with the cell sizes as in the embodiments described above.

The electrical circuitry to the two sets of electrodes is conventional, and the shocking electrodes can be pulsed in the same manner as those of conventional cuvettes in any of the gene pulsers that are commercially available as of the filing date of this application.

What is claimed is:

1. A cuvette for electroporation of membranous structures of nonuniform size, said cuvette comprising a vessel having a longitudinal axis, a pair of positioning electrodes spaced apart along said longitudinal axis, and a pair of electroporation electrodes spaced apart on opposite sides of said longitudinal axis, said electroporation electrodes being elongated and non-parallel to define a gap decreasing in width along said longitudinal axis.

2. The cuvette of claim 1 wherein each of said electroporation electrodes has a straight centerline, both said centerlines being co-planar with said longitudinal axis and forming an angle of from about 1 degree to about 45 degrees with each other.

3. The cuvette of claim 2 wherein said angle is from about 5 degrees to about 30 degrees.

4. The cuvette of claim 1 further comprising a sieving membrane spanning said cuvette and transverse to said longitudinal axis.

5. The cuvette of claim 1 further comprising a plurality of sieving membranes of different pore sizes spanning said cuvette, each said sieving membrane oriented transverse to said longitudinal axis, said sieving membranes spaced apart along said longitudinal axis and decreasing in pore size along said longitudinal axis in the same direction as said decreasing gap width.

6. The cuvette of claim 5 comprising two to five of said sieving membranes.

7. A method for transfecting a population of membranous structures of non-uniform size with exogenous species, said method comprising:
   (a) charging a cuvette with a suspension of said population in a liquid medium in which are dissolved said exogenous species, said cuvette comprising a vessel having a longitudinal axis, a pair of positioning electrodes spaced apart along said longitudinal axis, and a pair of electroporation electrodes spaced apart on opposite sides of said longitudinal axis, said electroporation electrodes being elongated and non-parallel and thereby defining a gap decreasing in width along said longitudinal axis;
   (b) energizing said positioning electrodes to distribute said membranous structures within said cuvette substantially according to size in the direction of said longitudinal axis, decreasing in size in the same direction as said decreasing gap width; and
   (c) with said membranous structures so distributed, energizing said electroporation electrodes to cause transfection of said exogenous species into said membranous structures.

8. The method of claim 7 wherein said cuvette is filled with a buffer solution prior to step (a), step (a) comprises loading said membranous structures at an end of said longitudinal axis where said gap width is greatest, and step (b) comprises imposing an electric potential between said electroporation electrodes of a magnitude that will effect said distribution by causing differential migration rates of said membranous structures through said buffer solution.

9. The method of claim 7 wherein said cuvette contains a sieving matrix, step (a) comprises placing said membranous structures over said sieving matrix at an end of said longitudinal axis where said gap width is greatest, and step (b) comprises imposing an electric potential between said electroporation electrodes of a magnitude that will effect said distribution by causing differential migration rates of said membranous structures through said sieving matrix.

10. The method of claim 7 wherein a sieving membrane is mounted to said cuvette, spanning said cuvette transverse to said longitudinal axis, step (a) comprises loading said membranous structures at an end of said longitudinal axis where said gap width is greatest, and step (b) comprises imposing an electric potential between said electroporation electrodes of a magnitude that will effect said distribution by sieving said membranous structures through said sieving membrane.

11. The method of claim 7 wherein a plurality of sieving membranes of different pore sizes are mounted to said cuvette, spanning said cuvette transverse to and spaced apart along said longitudinal axis, successively decreasing in pore size concurrently with said decreasing gap width, step (a) comprises loading said membranous structures at an end of said longitudinal axis where said gap width is greatest, and step (b) comprises imposing an electric potential between said electroporation electrodes of a magnitude that will effect said distribution by causing said membranous structures to migrate only as far as sieving membranes with pores sufficiently small to block further migration.

12. The method of claim 7 wherein each of said electroporation electrodes has a straight centerline, both said centerlines being co-planar with said longitudinal axis and forming an angle of from about 1 degree to about 45 degrees with each other.

\* \* \* \* \*